US006200341B1

United States Patent
Jones et al.

(10) Patent No.: US 6,200,341 B1
(45) Date of Patent: Mar. 13, 2001

(54) MECHANICAL HEART VALVE ASSEMBLY WITH SUPER-ELASTIC LOCK WIRE

(75) Inventors: Melanie E. Jones; Timothy A. Kelley, both of Round Rock, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/161,045

(22) Filed: Sep. 25, 1998

(51) Int. Cl.[7] .................................................. A61F 2/24

(52) U.S. Cl. ................................... 623/2.39; 623/2.1

(58) Field of Search .............................. 623/2, 2.1, 2.28, 623/2.38, 2.39, 2.4, 2.41

(56) References Cited

U.S. PATENT DOCUMENTS

| | | | |
|---|---|---|---|
| 3,371,352 | 3/1968 | Siposs et al. | 3/1 |
| 3,464,065 | 9/1969 | Cromie et al. | 3/1 |
| 3,587,115 | 6/1971 | Shiley et al. | 3/1 |
| 3,628,535 | 12/1971 | Ostrowsky et al. | . |
| 4,233,690 | * 11/1980 | Aikins | 623/2 |
| 4,535,483 | * 8/1985 | Klawitter et al. | 623/2 |
| 4,655,218 | 4/1987 | Kulik et al. | 128/321 |
| 4,683,883 | 8/1987 | Martin et al. | 128/303 |
| 4,743,253 | * 5/1988 | Magladry | 623/2 |
| 4,982,727 | 1/1991 | Sato | 128/4 |
| 5,035,709 | * 7/1991 | Wieting et al. | 623/2 |
| 5,120,308 | 6/1992 | Hess | 604/95 |
| 5,234,447 | 8/1993 | Kaster et al. | 606/153 |

(List continued on next page.)

OTHER PUBLICATIONS

Informational Brochure:Snowden Pencer, Diamond–Flex Surgical Instruments.
Informational Brochure:S.S. White Technologies Inc., Ready–Flex Standard Flexible Shafts and Ratio Drives.
Jansen, et al. "Detachable Shape–Memory Sewing Ring for Heart Valves", Artif Organs, vol. 15, No. 3, 1992, pp. 294–297.
Duerig, T. W., et al. Superelastic Nitinol for Medical Devices, Medical Plastics and Biomaterials, Mar./Apr. 1997, pp. 30–43.
Internet Article: Hodgson, D. E., et al., Shape Memory Alloys, Shape Memory Allocations, Inc., pp. 1–11.
Internet Article: Applications of Shape Memory and Super-elastic Alloys, Shape Memory Applications, Inc., pp. 1–2.
Internet Article: NITI Technical Information,Shape Memory Applications, Inc., pp. 1–2.
Internet Article: Glossary of NITI Terminology,NiTi Smart Sheet, pp. 1–2.
Internet Article: Introduction to Shape Memory and Super-elasticity,NiTi Smart Sheet, pp. 1–2.
Internet Article: Selected Properties of NITI,NiTi Smart Sheet, pp. 1–2.
Internet Article: Two–Way Memory,NiTi Smart Sheet, pp. 1–2.
Internet Article: Biocompatibility of NITI, NiTi Smart Sheet, pp. 1–2.

(List continued on next page.)

Primary Examiner—Michael J. Milano
Assistant Examiner—Alvin Stewart
(74) Attorney, Agent, or Firm—Timothy L. Scott; Phillip S. Lyren; Kenneth S. Barrow

(57) ABSTRACT

A mechanical heart valve assembly includes an orifice coupled with a stiffening ring and sewing cuff by a lock wire. The lock wire is made from a super-elastic material, e.g., a nickel-titanium alloy, and pre-formed into a C-shape. The lock wire is inserted between the orifice and stiffening ring by piercing the sewing cuff that surrounds the ring, and passing the lock wire into a window in the stiffening ring and into the aligned lock wire grooves on the stiffening ring and orifice. Once seated in the lock wire grooves, the lock wire retains its C-shape, providing a secure coupling between the orifice and stiffening ring.

12 Claims, 2 Drawing Sheets

U.S. PATENT DOCUMENTS

| | | | |
|---|---|---|---|
| 5,236,450 | | 8/1993 | Scott .......................................... 623/2 |
| 5,397,346 | * | 3/1995 | Walker et al. ............................. 623/2 |
| 5,397,351 | | 3/1995 | Pavenik et al. .......................... 623/11 |
| 5,403,305 | | 4/1995 | Sauter et al. ............................... 606/1 |
| 5,409,478 | | 4/1995 | Gerry et al. ............................... 606/1 |
| 5,443,502 | | 8/1995 | Caudillo et al. ........................... 623/2 |
| 5,531,785 | | 7/1996 | Love et al. ................................ 623/2 |
| 5,554,185 | | 9/1996 | Block et al. ............................... 623/2 |
| 5,571,175 | * | 11/1996 | Vanney et al. ............................. 623/2 |
| 5,582,607 | | 12/1996 | Lackman ................................... 606/1 |
| 5,609,601 | | 3/1997 | Kolesa et al. ......................... 606/170 |
| 5,707,380 | | 1/1998 | Hinchliffe et al. ................... 606/153 |
| 5,709,335 | | 1/1998 | Heck ................................. 227/176.1 |
| 5,716,370 | | 2/1998 | Williamson, IV et al. ........... 606/153 |
| 5,766,240 | * | 12/1998 | Johnson .................................... 623/2 |
| 5,843,177 | * | 12/1998 | Vanney et al. ............................. 623/2 |

OTHER PUBLICATIONS

Internet Article: Setting Shapes in NITI, NiTi Smart Sheet, p. 1.

Internet Article: Making Shape Memory Springs, NiTi Smart Sheet, pp. 1–2.

Internet Article: NITI Actuator Wire Properties,NiTi Smart Sheet, pp. 1–2.

Internet Article: Comparison of Properties of NITI and Stainless Steel, NiTi Smart Sheet, p. 1.

Internet Article: Approximate Surface Strains in Wire, Ribbon and Sheet, NiTi Smart Sheet, pp. 1–2.

Internet Article: Measuring Transformation Temperatures in NITI Alloys, NiTi Smart Sheet, pp. 1–3.

Internet Article: Transformation Temperature Hysteresis in NITI Alloys, NiTi Smart Sheet, pp. 1–2.

Internet Article: Selected NITI References,pp. 1–3.

Internet Article: SMA, Inc. Products and Services,Shape Memory Applications, Inc., pp. 1–4.

Internet Article: Lin, Richard, Shape Memory Alloys and Their Applications,pp. 1–6.

Internet Article: MedicalGuideWires,p. 1.

Internet Article: MedicalGuidePins,p. 1.

Internet Article: BendableSurgicqlTools, p. 1.

* cited by examiner

MECHANICAL HEART VALVE ASSEMBLY WITH SUPER-ELASTIC LOCK WIRE

BACKGROUND OF THE INVENTION

The present invention relates to a mechanical heart valve and method for manufacturing the same.

Mechanical heart valves are used to replace native valves which no longer function properly due to disease or other factors. Mechanical valves typically include an orifice having one or more occulders, which regulate blood flow. Also, mechanical valves typically include a stiffening ring that helps the valve assembly resist the compressive annular loads to which it is exposed when implanted. The stiffening ring can be made integral to the valve orifice or mechanically attached to the valve orifice.

When the stiffening ring is mechanically attached to the valve orifice, a coupling mechanism is required. One coupling mechanism includes a lock wire. For example, the family of Sulzer Carbomedics Prosthetic Heart Valves utilize a titanium lock wire positioned in grooves on the outer wall of the orifice and inner wall of the stiffening ring. A window in the stiffening ring allows insertion of the lock wire when the groove on the orifice is aligned with the groove on the stiffening ring.

Typically, the stiffening ring is incorporated with the sewing cuff. Therefore, in order to perform the mechanical attachment of orifice and ring, the cuff must be cut or otherwise partially disassembled to allow the lock wire to be passed through the window of the stiffening ring and into the aligned grooves. Once the lock wire is inserted, the cuff must be stitched closed again. This process of cutting and repairing the sewing cuff is time consuming. Further, this process leads to rejection of valve assemblies due to visual discrepancies caused by the cut/sew process.

Therefore, there is a need for a mechanical heart valve assembly and method for manufacturing, which reduces the manufacturing time and reduces the rejection of valve assemblies due to visual discrepancies.

SUMMARY OF THE INVENTION

The present invention is directed toward a mechanical heart valve assembly. The mechanical heart valve assembly includes a generally annular valve orifice. The outer surface of the valve orifice has a circumferential lock wire groove. A generally annular valve support ring surrounds at least a portion of the valve orifice. The support ring includes an inner surface with a circumferential lock wire groove. The orifice lock wire groove and support ring lock wire groove are positioned generally opposite each other. A lock wire is positioned in the grooves, operably coupling the orifice and support ring.

The lock wire comprises a super-elastic material. In one embodiment, the lock wire comprises nickel-titanium alloy, e.g., SE508 alloy. The lock wire includes a first and a second end and is generally "C" shaped. In one embodiment, the distance between the first and second ends of the lock wire is about 0.115 inches. In one embodiment, the lock wire has a cross-sectional diameter of about 0.0135 inches.

The support ring includes a window for receiving the wire. In one embodiment, a sewing cuff is disposed circumferentially about at least a portion of the support ring, covering the window.

Additionally, the present invention is directed toward a method of manufacturing a mechanical heart valve assembly. The mechanical heart valve assembly includes an orifice, a stiffening ring, and a lock wire. The lock wire is formed into a super-elastic "C" shape. The stiffening ring is aligned with the orifice so that the stiffening ring surrounds at least a portion of the orifice and so that a lock wire groove on an inner wall of the stiffening ring is generally aligned with a lock wire groove on an outer wall of the orifice. A first end of the lock wire is inserted through a window in the stiffening ring and into the generally aligned lock wire grooves until all of the lock wire is seated in the lock wire grooves.

In one embodiment, a sewing cuff is positioned circumferentially about at least a portion of the stiffening ring. The first end of the lock wire pierces the sewing cuff before it is inserted into the window of the support ring.

The present invention provides several advantages. First, there is no need to cut or otherwise disassemble the sewing cuff in order to insert the lock wire. Consequently, the number of manufacturing steps is reduced and the number of rejections based on visual discrepancies in the cuff is reduced. Both of these reductions help lower the manufacturing cost of the heart valve assembly. Additionally, the super-elastic lock wire is relatively easy to insert and returns to its memory shape when seated in the lock wire grooves. The lock wire will retain its pre-formed shape in a wide range of temperatures and after repeated sterilizations.

DETAILED DESCRIPTION OF THE EMBODIMENTS

Figure 1:
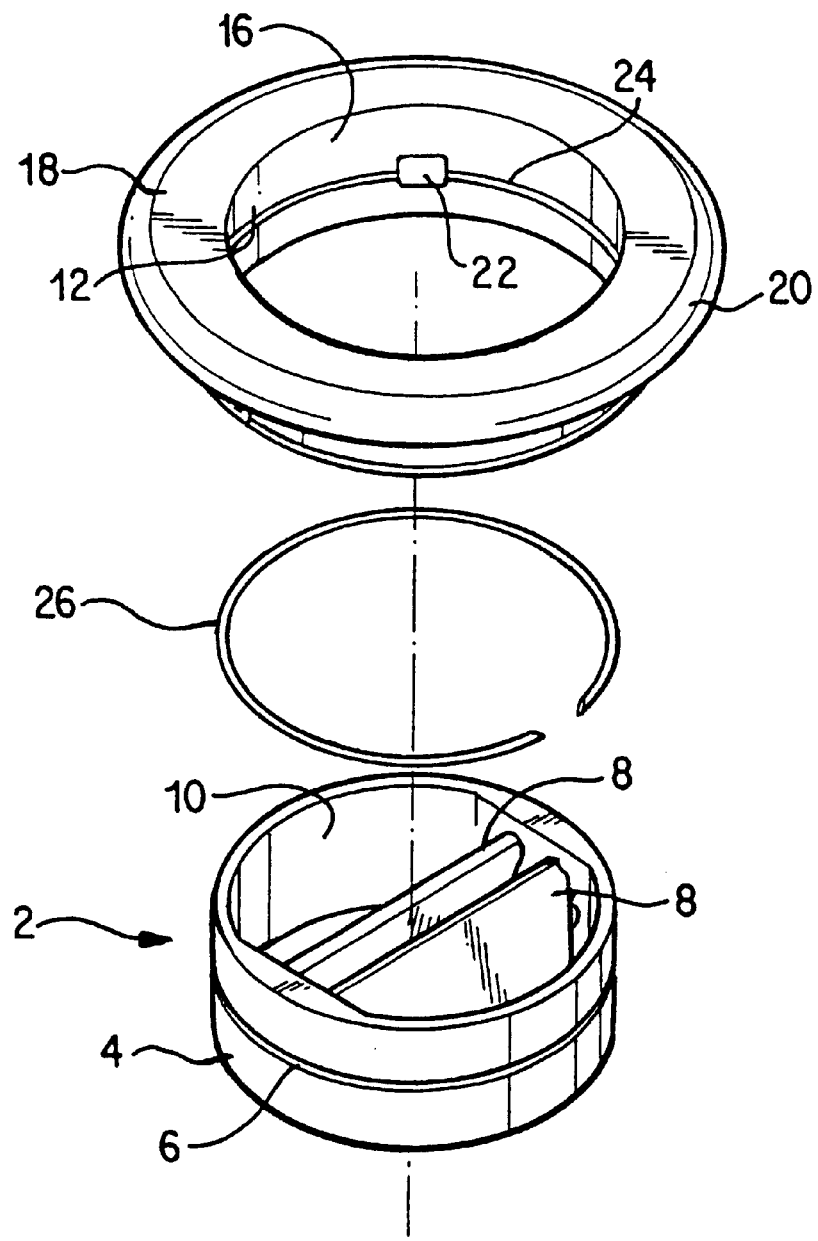
FIG. 1 is an exploded view of a mechanical heart valve assembly.

An exploded view of a mechanical heart valve assembly is shown in FIG. 1. A generally annular valve orifice 2 includes an outer wall 4 having a circumferential lock-wire groove 6. Occluders 8 are disposed within valve orifice 2 and coupled with inner wall 10. The embodiment shown in FIG. 1 includes two occluders 8. Other embodiments may include one occluder or three or more occluders.

Figure 2:
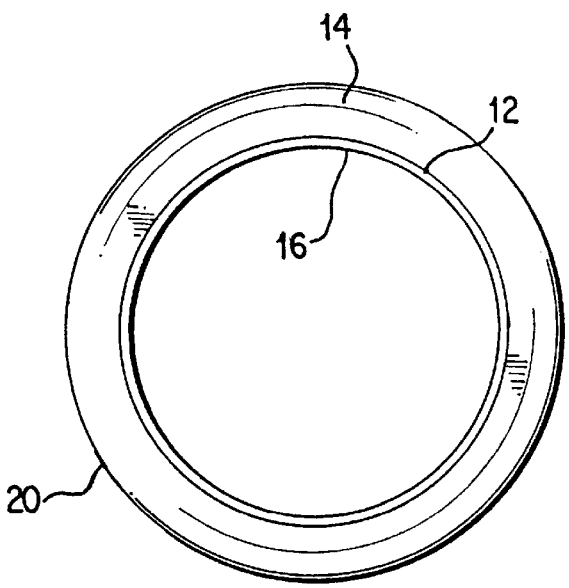
FIG. 2 is bottom view of a stiffening ring.

A generally annular stiffening or support ring 12 includes an outer wall 14 (FIG. 2) and an inner wall 16. In the embodiment shown in FIG. 1, a sewing cuff 20 includes a seating lip or flange 18 that is useful for seating the heart valve assembly in a valve annulus. Other embodiments include a sewing cuff 20 without a flange. As shown in FIG. 2, the sewing cuff 20 is positioned circumferentially around outer wall 14. When the heart valve assembly is seated in a native valve annulus, sutures are passed through cuff 20 and the surrounding annulus tissue to securely fix the valve assembly in place. Cuff 20 is made from polyester knit, PTFE knit, ePTFE knit, or other biocompatible material that promotes tissue growth about the valve assembly, providing a long-term, secure attachment.

Stiffening ring 12 also includes window 22 extending from outer wall 14 to inner wall 16. A circumferential lock-wire groove 24 on inner wall 16 intersects window 22, as shown in FIG. 1. Lock wire 26 mechanically couples orifice 2 and stiffening ring 12 as described below. Lock wire 26 is made from a biocompatible, super-elastic material. In one embodiment, lock wire 26 is made from a nickel titanium alloy, commonly known as nitinol. One example of a suitable alloy is SE508 alloy available from Nitinol Devices & Components, Inc., Fremont, Calif.

Figure 3:
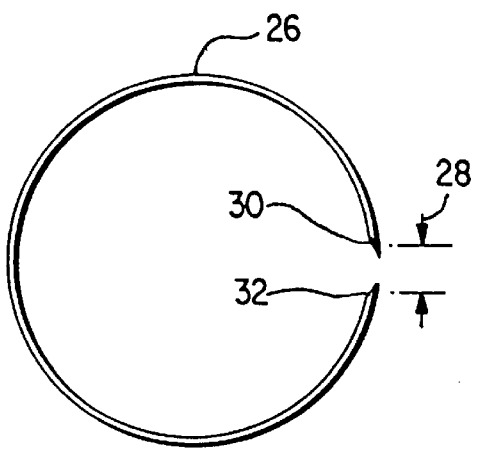
FIG. 3 is a top view of a lock wire.
Figure 4:
FIG. 4 is a side, cross-sectional view of a lock wire.

Referring to FIG. 3, the pre-formed of lock wire 26 is generally in the shape of a "C". The length of wire 26 is selected for the specific size of the valve being used, and the gap 28 in lock wire 26, which defines the open part of the "C" shape, is about 0.115 inches. For example, a valve sized for a 29-mm annulus has a lock wire with a length of about 3.0203 inches and gap of about 0.115 inches. Referring to the embodiment shown in FIG. 4, the cross-sectional shape of lock wire 26 is generally circular with a diameter of about 0.0135 inches +/–0.0005 inches.

The manufacturing process of a heart valve assembly according to the present invention is as follows. First, lock wire 26 is pre-formed into a C-shaped ring of the appropriate diameter for the selected valve size. This is accomplished by wrapping the generally straight lock wire around a rod of appropriate diameter and annealing the lock wire into the desired "C" shape. Other methods for working with super-elastic materials may also be used.

Stiffening ring 12 is disposed about orifice 2 so that lock wire grooves 6, 24 are generally aligned. One end 30 or 32 of lock wire 26 is used to pierce cuff 20. The end then passes through cuff 20 into window 22 of stiffening ring 12. Lock wire 26 then slides into the generally opposed grooves 6, 24 and passes around the circumference of both stiffening ring 12 and orifice 2 in grooves 6, 24. When lock wire 26 is fully inserted in grooves 6, 24 it returns to its pre-formed "C" shape, providing a secure mechanical coupling between orifice 2 and stiffening ring 12. Since cuff 20 has been pierced by wire having a small diameter, e.g., 0.0135 inches, there is no significant damage to cuff 20 that might require repair.

Due to the super-elastic characteristics of lock wire 26, it will retain its shape within the physiological temperature range commonly found in an implantation. In the embodiment using the SE508 alloy, the lock wire will retain its shape to temperatures as low as 20 degrees Celsius. Further, the lock wire will retain its shape after multiple steam sterilizations to which it may be exposed during manufacture and prior to implantation.

Other embodiments are within the scope of the following claims.

We claim the following:

1. A mechanical heart valve assembly comprising:
   a generally annular valve orifice, said orifice having an outer surface comprising a circumferential groove;
   a generally annular valve support ring surrounding at least a portion of said valve orifice, said support ring having an inner surface comprising a circumferential groove, wherein said orifice groove and said support ring groove are generally opposite each other;
   a sewing cuff disposed circumferentially about at least a portion of said support ring; and
   a lock wire positioned in said grooves and operably coupling said orifice and said support ring, said lock wire comprising a super-elastic material and having a cross section, wherein said lock wire is inserted into said grooves through a hole in said sewing cuff substantially the same size as said cross section of said lock wire.

2. The assembly of claim 1, wherein the lock wire comprises nickel-titanium alloy.

3. The assembly of claim 1, wherein the lock wire includes a first and a second end and is generally "C" shaped.

4. The assembly of claim 3, wherein the distance between the first and second ends of the lock wire is about 0.115 inches.

5. The assembly of claim 1, wherein the lock wire has a cross-sectional diameter of about 0.0135 inches.

6. The assembly of claim 1, wherein the support ring includes a window.

7. A method of manufacturing a mechanical heart valve assembly comprising a valve orifice, a stiffening ring, a sewing cuff disposed around said stiffening ring and comprising a flexible biocompatible material, and a lock wire comprising a super-elastic material and having a cross section and a first end, the steps comprising:
   forming said lock wire into a pre-formed "C" shape;
   aligning said stiffening ring and said sewing ring with said orifice so that said stiffening ring surrounds at least a portion of said orifice and so that a lock wire groove on an inner wall of the stiffening ring is generally aligned with a lock wire groove on an outer wall of the orifice;
   inserting a first end of the lock wire through said flexible material of said sewing cuff without creating a hole in said flexible material significantly larger than said cross section of said lock wire and
   inserting said first end of said lock wire through a window in the stiffening ring and into the generally aligned lock wire grooves until all of the lock wire is seated in the lock wire grooves.

8. The method according to claim 7 wherein the biocompatible material is a knit fabric and said lock wire is inserted through said fabric without cutting said fabric.

9. The method according to claim 8 wherein said first end of said lock wire is used to pierce said fabric.

10. The method according to claim 1 wherein the lock wire comprises nickel-titanium alloy.

11. The method according to claim 7 wherein said lock wire returns to its preformed "C" shape when it has been seated in the lock wire grooves.

12. A mechanical heart valve assembly constructed according to the method of claim 7.

* * * * *